US00PP08808P

United States Patent [19]

VandenBerg

[11] Patent Number: Plant 8,808

[45] Date of Patent: Jun. 28, 1994

[54] CHRYSANTHEMUM PLANT NAMED BLUE VOLARE

[75] Inventor: Cornelis P. VandenBerg, Salinas, Calif.

[73] Assignee: Yoder Brothers, Inc., Barberton, Ohio

[21] Appl. No.: 41,495

[22] Filed: Apr. 1, 1993

[51] Int. Cl.[5] ..... A01H 5/00

[52] U.S. Cl. ..... Plt./82.4

[58] Field of Search ..... Plt. 74.1, 82.4

[56] References Cited

U.S. PATENT DOCUMENTS 4,616,099 10/1986 Sparkes ..... 47/58.1

OTHER PUBLICATIONS

Sigurbjornsson, B., "Chapter 8, Induced Mutations", *Crop Breeding,* 1983, ASA, CSSA, pp. 153–176.

Broertjes, C., (1966) "Mutation Breeding of Chrysanthemums" *Euphytica* 15, pp. 156–162.

Broertjes, C., et al, (1980) "A Mutant of a Mutant of a Mutant of a . . . Irradiation of Progressive Radiation-Induced Mutants in a Mutation-Breeding Programme with *Chrysanthemum morifolium*", *Euphytica* 29:525–530.

Searle, S. A., et al., "Use of Gamma and X-Rays", *Chrysanthemums the Year Round,* 1958, Blandford Press, Ltd., London, pp. 27–29.

Dowrick, G. J., et al., (1966) "The Induction of Mutations in Chrysanthemums Using X and Gamma Radiations", *Euphytica* 15:204–210.

Machin, B. J., "Sporting and Irradiation" *The Chrysanthemum Manual,* 1979, The National Chrysanthemum Society, London, pp. 329–336.

Broertjes, C., et al., "Chrysanthemums" *Application of Mutation Breeding Methods in the Improvement of Vegetatively Propagated Crops,* 1978, Elsevier Scientific Pub. Co., N.Y., pp. 162–175.

Chan, A. P., (1966) "Chrysanthemum and Rose Mutations Induced by X Rays" Proceedings Amer. Soc. for Hort. Sci. 88 pp. 613–620.

*Primary Examiner*—James R. Feyrer

*Attorney, Agent, or Firm*—Foley & Lardner

[57] ABSTRACT

A chrysanthemum plant named Blue Volare particularly characterized by its flat capitulum form; daisy capitulum type; purple ray floret color; diameter across face of capitulum of 80 to 83 mm when fully opened, when grown as a single stem spray cut mum; photoperiodic flowering response of 47 to 54 days after start of short days when grown in Salinas, Calif.; flowering response in Bogota, Colombia is 67 to 70 days; plant height is 76 to 84 cm when grown in Salinas with 3 to 11 long days prior to start of short days; height is 107 to 114 cm when grown in Bogota with 14 to 15 long days prior to start of short days; peduncle length of the first lateral at flowering after removing the apical bud and without growth regulator applications is 10 to 15 cm when grown in Salinas, and 13 to 18 cm when grown in Bogota; peduncle length of the fourth lateral at flowering is 13 to 18 cm when grown in Salinas, and 18 to 23 cm when grown in Bogota; and excellent tolerance to low night temperatures for bud initiation and flower development.

1 Drawing Sheet

The present invention comprises a new and distinct cultivar of Chrysanthemum, botanically known as *Dendranthema grandiflora,* and referred to by the cultivar name Blue Volare.

Blue Volare, identified as 3550 (87-512B13), is a product of a mutation induction program. The new cultivar was discovered and selected by Cornelis P. VandenBerg on Nov. 28, 1990, in a controlled environment in Salinas, Calif., as one flowering plant within a flowering block established as rooted cuttings from stock plants which had been exposed as unrooted cuttings to an X-ray source of 1500 rads in Fort Myers, Fla., on Jun. 28, 1990.

The irradiated parent cultivar was the cultivar identified as Volare, disclosed in U.S. Plant Pat. No. 8,058, and described as a spray cut mum with flat capitulum form; daisy capitulum type; light purple ray floret color; diameter across face of capitulum of 80 to 83 mm when fully opened; flowering response period of 49 to 53 days after start of short days in Salinas, Calif., and 63 to 72 days in Bogota, Colombia; plant height of 74 to 99 cm when grown in Salinas with 3 to 14 long days prior to start of short days, and 99 to 114 cm when grown in Bogota with 14 to 21 long days prior to start of short days; and excellent tolerance to low night temperatures for bud initiation and flower development. The foregoing description of Volare has a somewhat wider range of measurements than the description of Volare in the noted plant patent. This is based on continued flowering trials of Volare after the patent application for Volare was prepared and filed.

The irradiation program resulting in Blue Volare had as its primary objective the expansion of ray floret color ranges of the parent cultivar Volare. The irradiation program comprised irradiating cuttings of the parent cultivar at irradiation levels of 1500, 1750 and 2000 rads. A total of 1414 cuttings harvested from a total of 225 irradiated plants were planted on Sep. 24, 1990, Sep. 17, 1990 and Sep. 17, 1990, respectively. Of these, 7 initial selections were made, which selections were then revegetated and reflowered. Three consecutive flowerings resulted in discarding 4 of the original 7 selections on Aug. 9, 1991, while 3 codes were retained as PI (Possible Introduction) status. The three retained codes were further tested in Salinas, Calif., and in Bogota, Colombia, ultimately resulting in the decision to introduce two of the remaining selections as Blue Volare and Light Volare. The third remaining selection was discraded on Oct. 26, 1992. The cultivar Light Volare is disclosed in a pending application.

The first act of asexual reproduction of Blue Volare was accomplished when vegetative cuttings were taken from the original selection in January 1991 in a controlled environment in Salinas, Calif., by technicians working under supervision of Cornelis P. VandenBerg.

Horticultural examination of controlled flowerings of successive plantings has shown that the unique combination of characteristics as herein disclosed for Blue Volare are firmly fixed and are retained through successive generations of asexual reproduction.

Blue Volare has not been observed under all possible environmental conditions. The phenotype may vary significantly with variations in environment such as temperature, light intensity and daylength, without, however, any variance in genotype.

The following observations, measurements and comparisons describe plants grown in Salinas, Calif. and in Bogota, Colombia, under greenhouse conditions which approximate those generally used in commercial greenhouse practice. The low night temperature tolerance was determined in repeated flowerings in Bogota, Colombia, at temperatures as low as 5°-10° C.

The following traits have been repeatedly observed and are determined to be basic characteristics of Blue Volare, which, in combination, distinguish this Chrysanthemum as a new and distinct cultivar:

1. Flat capitulum form.
2. Daisy capitulum type.
3. Purple ray floret color.
4. Diameter across face of capitulum of 80 to 83 mm when fully opened, when grown as a single stem spray cut mum.
5. Photoperiodic flowering response to short days when grown in Salinas, Calif., is 47 to 54 days after start of short days. Flowering response in Bogota, Colombia is 67 to 70 days.
6. Plant height is 76 to 84 cm when grown in Salinas with 3 to 11 long days prior to start of short days; height is 107 to 114 cm when grown in Bogota with 14 to 15 long days prior to start of short days.
7. Peduncle length of the first lateral at flowering after removing the apical bud and without growth regulator applications is 10 to 15 cm when grown in Salinas, and 13 to 18 cm when grown in Bogota. Peduncle length of the fourth lateral at flowering is 13 to 18 cm when grown in Salinas, and 18 to 23 cm when grown in Bogota.
8. Excellent tolerance to low night temperatures for bud initiation and flower development.

The accompanying color photographic drawing is a front perspective view of a single stem cut spray mum of Blue Volare, with the colors being as nearly true as possible with illustrations of this type.

Of the commercial cultivars known to the inventor, the most similar in comparison to Blue Volare is the parent cultivar Volare. All traits of Blue Volare are similar to those of Volare, except for the ray floret color and the plant height. The ray floret color of Blue Volare is a significantly darker purple than the ray floret color of Volare. In several flowering trials the plant height of Blue Volare was 3 to 8 cm taller than the plant height of Volare.

In the following description color references are made to the Royal Horticultural Society Colour Chart. The color values were determined on plant material grown as a pinched spray pot mum in Salinas, Calif. on Dec. 16, 1992.

Classification:

*Botanical.*—*Dendranthema grandiflora* cv Blue Volare.

*Commercial.*—Flat daisy cut spray mum.

INFLORESCENCE

A. Capitulum:

*Form.*—Flat.

*Type.*—Daisy.

*Diameter across face.*—80 to 83 mm when fully opened.

B. Corolla of ray florets:

*Color (general tonality from a distance of three meters).*—Purple.

*Color (upper surface).*—75A, overcast with 80D.

*Color (under surface).*—75B to 75C.

*Shape.*—Straight, slightly ribbed.

C. Corolla of disc florets:

*Color (mature).*—14B.

*Color (immature).*—144B.

D. Reproductive organs:

*Androecium.*—Present on disc florets only; moderate pollen.

*Gynoecium.*—Present on both ray and disc florets.

PLANT

A. General appearance:

*Height.*—76 to 84 cm when grown in Salinas with 3 to 11 long days prior to start of short days; height is 107 to 114 cm when grown in Bogota with 14 to 15 long days prior to start of short days.

B. Foliage:

*Color (upper surface).*—147A.

*Color (under surface).*—147B.

I claim:

1. A new and distinct Chrysanthemum plant named Blue Volare, as described and illustrated.

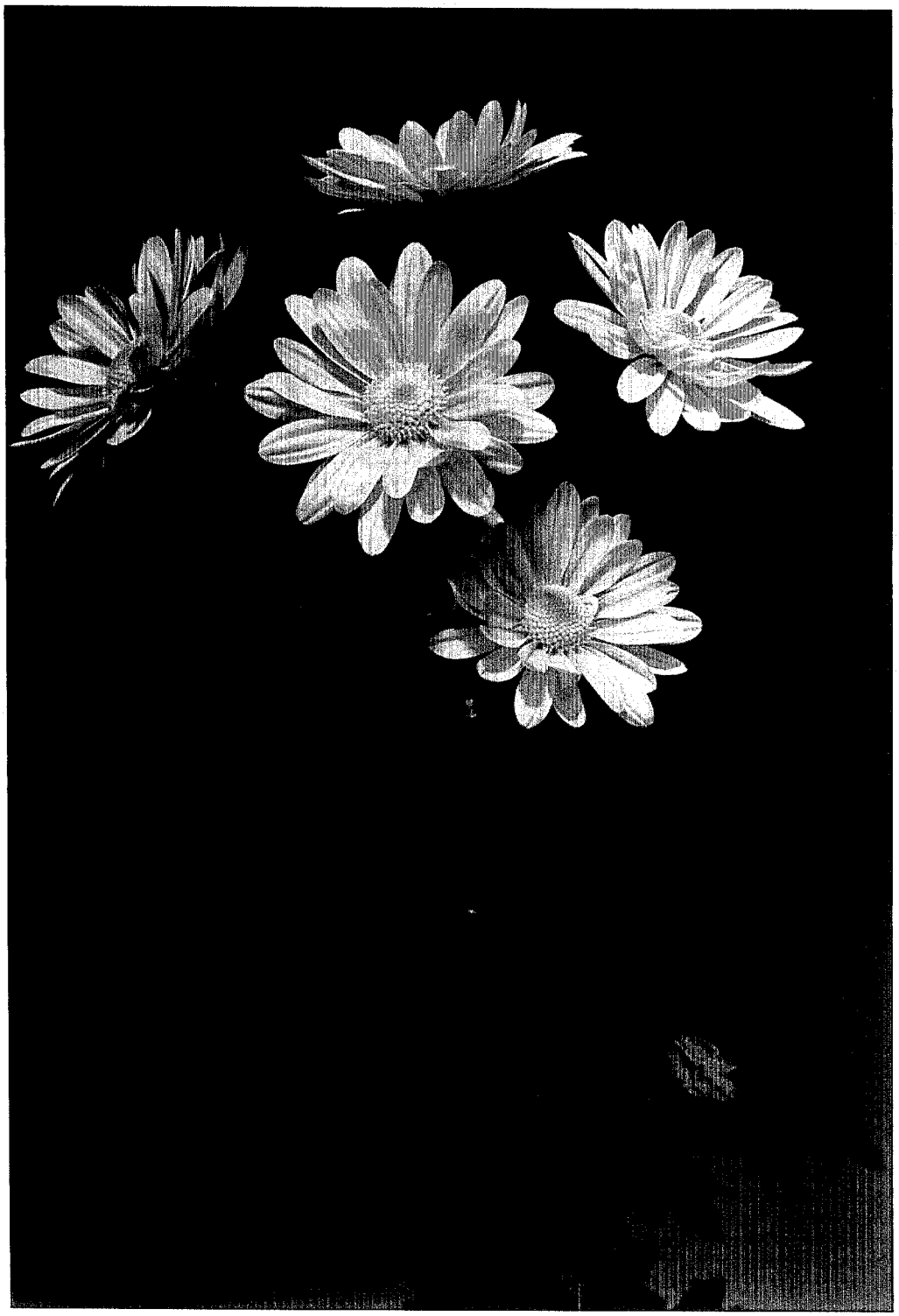

* * * * *